United States Patent [19]
Daniele et al.

[11] Patent Number: 6,014,851
[45] Date of Patent: Jan. 18, 2000

[54] PACKAGE FEED ARRANGEMENT IN A MACHINE FOR THE AUTOMATED PACKAGING OF NEEDLES AND ATTACHED SUTURES

[75] Inventors: Robert A. Daniele, Flemington; Anthony Esteves, Somerville, both of N.J.; George Horst Reinemuth, Glen Mills; Richard Paul Branco, Collegeville, both of Pa.

[73] Assignee: Ethicon, Inc., Somerville, N.J.

[21] Appl. No.: 09/020,092

[22] Filed: Feb. 6, 1998

[51] Int. Cl.[7] ..................................................... B65B 63/04
[52] U.S. Cl. ................................. 53/430; 53/467; 53/473; 53/478; 53/118; 53/250; 53/267; 53/281
[58] Field of Search ............................... 53/430, 116, 118, 53/250, 467, 471, 473, 478, 235, 249, 253, 267, 281, 287, 297; 235/61; 269/64, 67, 69, 71

[56] References Cited

U.S. PATENT DOCUMENTS

| | | | |
|---|---|---|---|
| 2,620,028 | 12/1952 | Kohut | 163/5 |
| 2,746,118 | 5/1956 | Drummond et al. | 53/35 |
| 2,928,395 | 3/1960 | Forbes et al. | 128/335.5 |
| 3,167,895 | 2/1965 | Egler et al. | 28/21 |
| 3,298,681 | 1/1967 | Youngblood | 269/69 |
| 3,611,551 | 10/1971 | Shave et al. | 29/515 |
| 3,618,282 | 11/1971 | Hagel et al. | 53/21 |
| 3,798,422 | 3/1974 | Foret et al. | 235/61.11 R |
| 3,816,889 | 6/1974 | Crotti | 28/21 |
| 3,875,946 | 4/1975 | Duncan | 128/339 |
| 3,961,780 | 6/1976 | Saj | 269/64 |
| 3,980,177 | 9/1976 | McGregor | 206/63.3 |
| 4,011,155 | 3/1977 | Feuerstein et al. | 209/74 |
| 4,072,041 | 2/1978 | Hoffman et al. | 72/416 |
| 4,145,006 | 3/1979 | Webb | 269/69 |
| 4,226,098 | 10/1980 | Alexander | 69/2 |
| 4,255,917 | 3/1981 | Stone | 53/430 |
| 4,323,168 | 4/1982 | Callahan | 221/42 |
| 4,424,898 | 1/1984 | Thyen et al. | 206/63.3 |
| 4,595,186 | 6/1986 | Reed et al. | 269/69 |
| 4,643,410 | 2/1987 | Mudge et al. | 269/64 |
| 4,672,871 | 6/1987 | Gudmestad | 83/151 |
| 4,722,384 | 2/1988 | Matsutani | 163/1 |
| 4,832,025 | 5/1989 | Coates | 128/335.5 |
| 4,922,904 | 5/1990 | Uetake et al. | 606/226 |
| 5,056,658 | 10/1991 | Sobel et al. | 53/1 |
| 5,226,336 | 7/1993 | Coates | 83/170 |
| 5,230,424 | 7/1993 | Alpern et al. | 206/63.3 |
| 5,438,746 | 8/1995 | Demarest et al. | 29/564.6 |
| 5,469,689 | 11/1995 | Demarest et al. | 53/430 |
| 5,473,810 | 12/1995 | Demares et al. | 29/712 |
| 5,473,854 | 12/1995 | Demarest et al. | 53/430 |
| 5,477,609 | 12/1995 | Demarest et al. | 29/788 |
| 5,485,668 | 1/1996 | Demarest et al. | 29/517 |
| 5,487,212 | 1/1996 | Demarest et al. | 53/430 |
| 5,487,216 | 1/1996 | Demarest et al. | 29/705 |
| 5,500,991 | 3/1996 | Demarest et al. | 29/407.08 |
| 5,511,670 | 4/1996 | Demarest et al. | 209/540 |
| 5,664,404 | 9/1997 | Ivanov et al. | 53/430 |

FOREIGN PATENT DOCUMENTS

| | | |
|---|---|---|
| 428253 | 5/1991 | European Pat. Off. . |
| 581699 | 2/1994 | European Pat. Off. . |
| 2632850 | 12/1989 | France . |
| 89 04145.3 | 7/1989 | Germany . |
| 63-212027 | 9/1988 | Japan . |
| 63-299834 | 12/1988 | Japan . |

*Primary Examiner*—Joseph J. Hail, III
*Assistant Examiner*—Ed Tolan
*Attorney, Agent, or Firm*—Scully, Scott, Murphy & Presser

[57] ABSTRACT

A machine for the automated packaging of armed sutures or; in effect, surgical needles having sutures attached thereto and, more particularly, a package feed arrangement in an automated machine including a package tray supplying carousel arrangement and robotic pivot arm mechanism for the high-speed feed of package trays for the individualized packaging of single or individual surgical needles each having an attached suture into a tray and detachable cover providing a suture package utilized for the packaging of the individual or single needles and attached sutures.

28 Claims, 11 Drawing Sheets

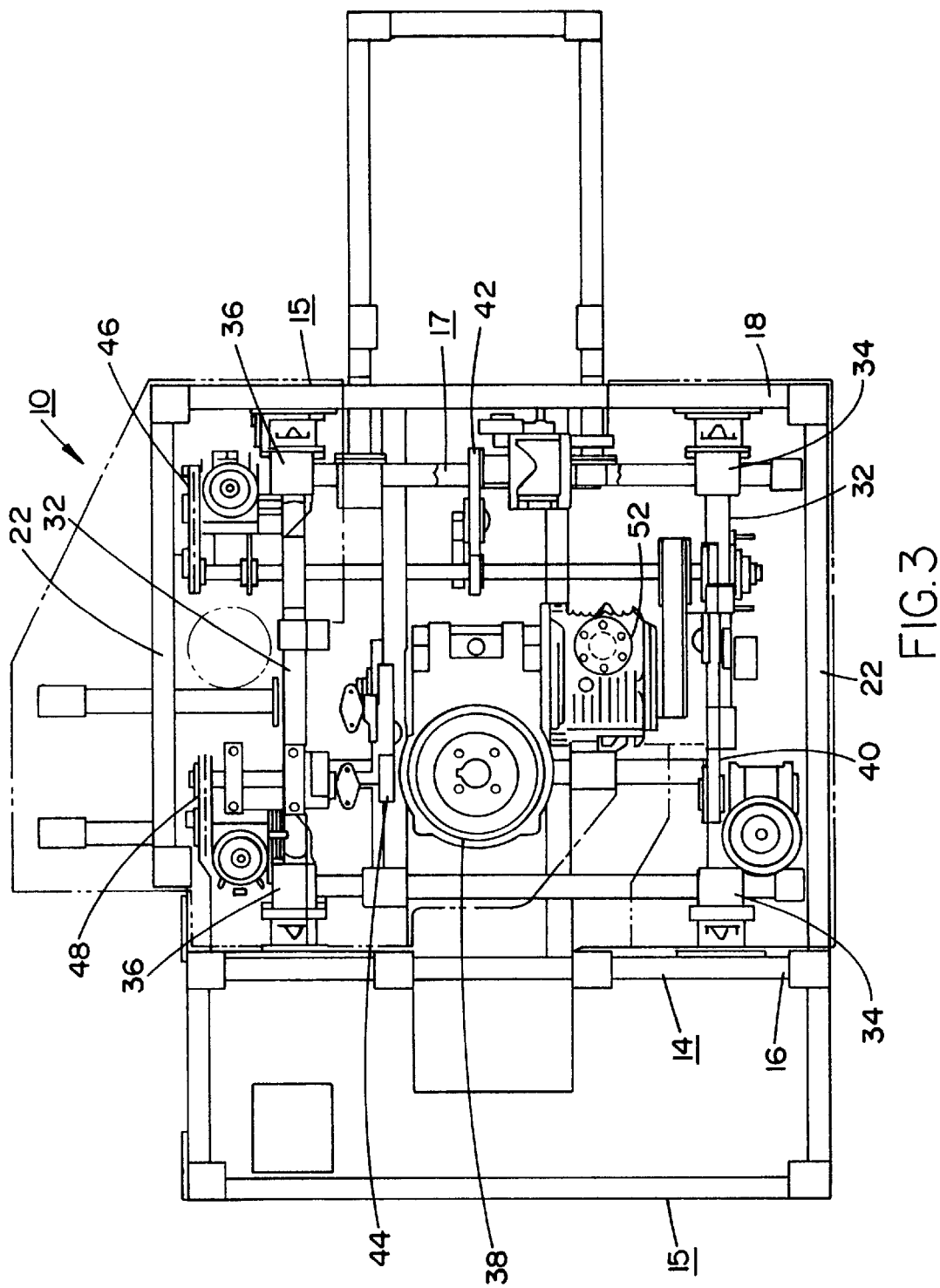

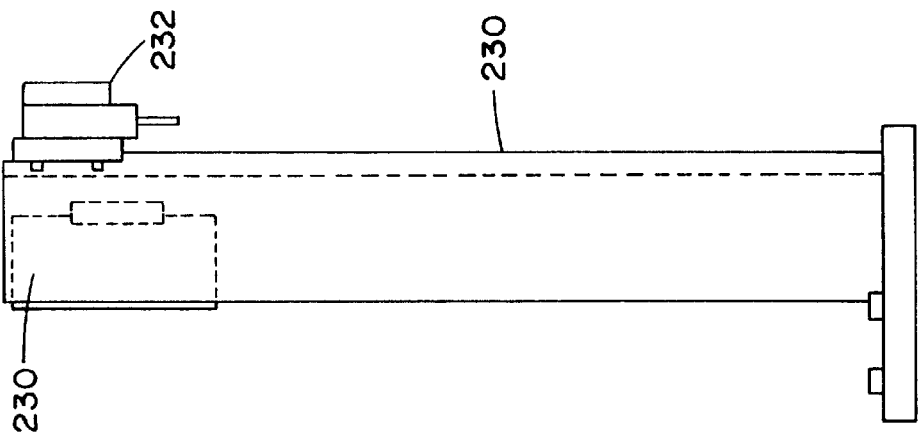
FIG.18
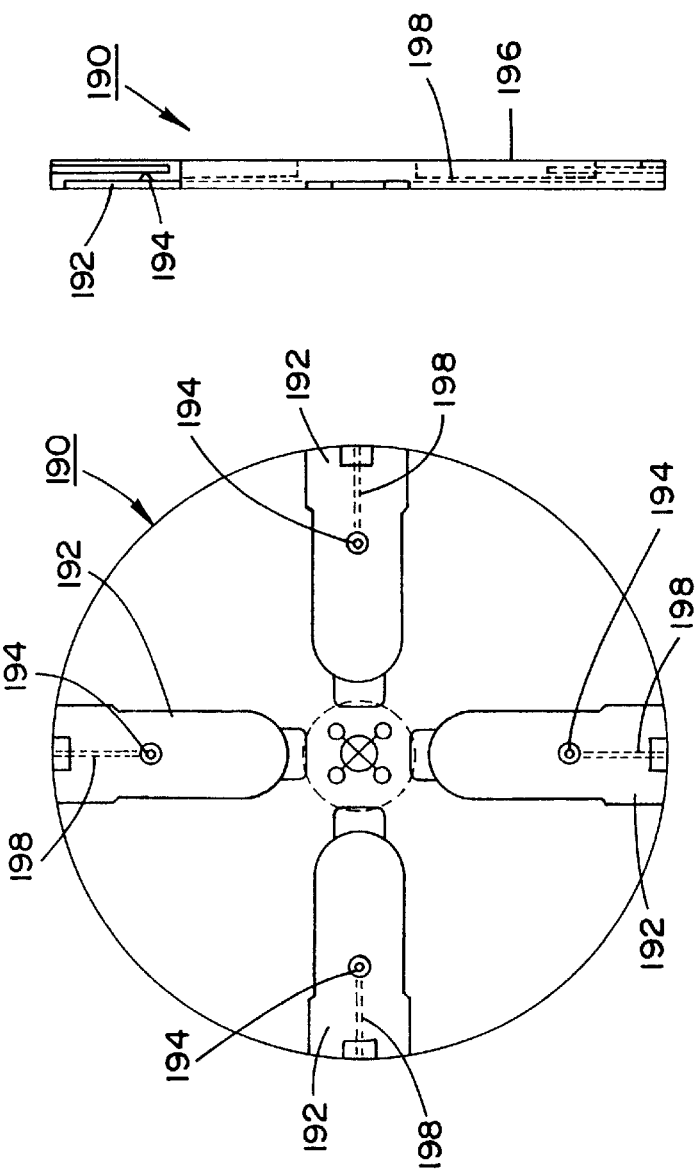
FIG.14
FIG.13

PACKAGE FEED ARRANGEMENT IN A MACHINE FOR THE AUTOMATED PACKAGING OF NEEDLES AND ATTACHED SUTURES

BACKGROUND OF THE INVENTION

1. Field of the Invention

The present invention relates to a machine for the automated packaging of armed sutures or; in effect, surgical needles having sutures attached thereto and, more particularly, pertains to a package feed arrangement in an automated machine for the high-speed individualized packaging of single or individual surgical needles each having an attached suture into a tray and detachable cover providing a suture package utilized for the packaging of the individual or single needles and attached sutures. Pursuant to the invention, the packages which are adapted for the receipt of surgical needles and attached sutures are sequently supplied to the packaging machine from a carousel containing stacks of empty packages and are transferred to the machine through the intermediary of robotic arm structure. The invention is also directed to a method for supplying the automated packaging machine with packages by employing the novel carousel end robotic transfer arm arrangement.

The automated packaging machine further incorporates operative mechanism adapted to wind the sutures into a peripheral channel of the tray and facilitating the attachment of the cover to the tray which contains the single needle and attached wound suture, and which cover concurrently constitutes a product-identifying label as a component of the tray. The cover being shaped such that removal of the cover is not necessary to enable a user to gain access to the contents of the tray; in essence, the armed suture.

The automated packaging machine also provides for a rotary turret or dial-like turntable for the high-speed loading thereof with empty trays; the sequential loading of successive forwardly indexed trays each with a needle and attached suture; the indexed advance of the needle and suture-filled tray to suture-winding stations of the machine; the conveyance of the trays each containing the needle and attached wound suture to a cover-applying station of the machine to provide the completed suture packages, and the further advance of the suture packages for subsequent automated removal of the completed suture packages from the machine. The automated packaging machine is resultingly adapted to provide for the continuous and repetitive production of suture packages in a single high-speed production cycle without necessitating any manual manipulation thereof.

In order to facilitate the production of the suture packages as described herein, the present invention provides for a plurality of sequential operating stations, in which a first station includes carousel structure having stacked package trays sequentially conveyed to a rotary plate element which slices off the bottommost package tray from a stack of trays, and includes operative structure for transferring the separated package tray to a tool nest mounted on a rotary dial for transfer to subsequent processing stations, where the package tray is provided with an armed suture, the suture wound into the package tray, a cover applied thereto to produce the completed product-containing package and which is then removed from the packaging machine and transported for additional processing and/or storage.

The present invention is also directed to the provision of a novel method for the automated supplying of package trays for the packaging of individual surgical needles and attached sutures into the trays, and to thereafter enable the application of covers thereto in sequential production steps through the intermediary of the automated packaging machine.

Currently, in the medical, surgical and health-related technology, the high-speed and efficient packaging of either single or multiple sutures which are each suitably attached to surgical needles, such as by being swaged or similarly fastened thereto, and in which such combined sets of needles and sutures are generally referred to as armed sutures, is imparted an increasing degree of importance in view of the rising demand of users for such combined surgical needles and attached sutures, and various diverse types of inexpensively manufactured suture packages for the containment of needles and attached sutures have been developed and are presently widely employed.

In specific instances, suture packages may be covered tray-shaped containers designed to receive and fixedly retain therein one or more needles and therewith attached sutures, in which the suture packages, upon opening of the covers, must enable the uncomplicated and simple withdrawal of a respective individual needle and its attached suture in a smooth unobstructed manner. In essence, when the needle which is to be removed from the suture package is engaged by a surgeon or health professional, for example, by being gripped through the intermediary of a forceps and then pulled out of the suture tray, it is essential that the needle easily disengage from its restraint in the package while the suture which is attached to the needle should also be readily able to slip out of the tray in the absence of any binding or snagging, and in the instance of the tray housing a plurality of armed sutures also without becoming entangled with other sutures still remaining in the suture tray or package. Thus, pursuant to a specific needle and suture package construction which, for example, may comprise an injection-molded plastic tray, the needles are generally engaged by clamping structure located in the tray so as to be "parked" or retained in predetermined position or array in a central region of the tray. The sutures extending from the needles to which they are attached are then conducted into and deposited in a peripheral channel formed within the suture tray so as to extend along the peripheral length of the channel. This positioning of the needles, and particularly that of the sutures within the peripheral channel of the tray is intended to eliminate tight bends or curves normally imposed on the sutures so as to facilitate their easy withdrawal from the suture package.

2. Discussion of the Prior Art

Until relatively recently, the introduction of needles with attached sutures into suture packages or molded plastic trays was being implemented in a substantially manual manner. In that instance, the needles were manually placed into the tray so as to be clampingly engaged by means of suitable needlegripping structure, and thereafter the attached sutures wound or positioned within the confines of the tray. Subsequently, a suitable cover was superimposed upon and fastened to the filled tray, and the resultant armed suture package conveyed to a suitable arrangement for possible sterilizing or further over wrapping.

The foregoing essentially manual and relatively basic process for winding the sutures into the tray, and especially the locating thereof into the peripheral channel of the tray during manipulation of the tray, was quite time-consuming, and in conjunction with the manual application of the cover into the tray in a basically individual or piece-by-piece mode, represented a serious hindrance to a large volume or mass produced manufacturing output, and adversely affected the economics in attempting to provide such large quantities of suture packages containing either single or multiple surgical needles and attached sutures.

As an improvement over the foregoing, there was then developed a generally semi-automated winder machine for packaging surgical needles and attached sutures in a tray-like suture package, and wherein at least some of the previously manually implemented packaging steps were to some extent automated in order to be able to increase the output of needle and suture-containing packages while simultaneously reducing the number of manual procedures in effectuating the packaging of those particular items.

To that effect, the semi-automated winder machine, although necessitating the manual orientation of the trays for implementing the filling thereof with needles and attached sutures, included a winding station which to a considerable degree automated the winding process for the sutures so as to place the latter into a peripheral channel extending about the circumference of the tray. Also provided was a further therewith operatively associated device which enabled covers to be manually placed on the needle and suture-filled trays to be fastened thereto by means of a pressing die forming latchingly engaging interconnections between each of the covers and the trays, while concurrently producing from a portion of the cover a product-identifying label which remains permanently attached to the tray upon subsequent detachment of the cover. Although providing a considerable advance over the state-of-the-art in the packaging of needles and sutures, the semi-automated winder machine nevertheless necessitated the implementation of a considerable number of manual and labor-intensive handling steps in effectuating the filling of the trays with surgical needles and attached sutures, attaching the cover and, generally, producing complete suture packages.

As a further technological advance over the foregoing semi-automated needle and suture package-forming concept, there was then developed a substantially fully automated packaging machine which is adapted, in a highly efficient and extremely rapid mode, to continually fill successive trays of the type described hereinabove with pluralities of surgical needles and attached sutures, and subsequently causing the sutures to be wound into the confines of the tray, such as into a peripheral channel extending about the tray. Thereafter, the packaging machine was designed to implement the automated positioning and fastening of covers to the needle and suture-filled trays to produce completed suture packages of the type described hereinabove, which were then adapted to be transported to a suitable locale for selective further processing, such as sterilizing, and/or over wrapping, as is required by this technology.

In particular, the automated packaging machine was designed to provide the packages with each housing a plurality of needles and attached sutures. For example, the packaging machine for accomplishing the foregoing, which is commonly assigned to the assignee of the present application, is described in U.S. Pat. Nos. 5,487,212; 5,473,854; 5,469,689; 5,473,810; 5,511,670; 5,452,636; 5,438,746; 5,500,991; 5,477,609; 5,485,668; and 5,487,216.

The flat, tray-shaped suture package produced by the packaging machine set forth in the above-mentioned patents provides for the storage therein of multiple surgical needles and attached sutures, while concurrently recognizing the need to facilitate the smooth and unobstructed withdrawal of individual needles and attached sutures from the suture package. For instance, such a suture package is disclosed in applicants' U.S. Pat. No. 5,230,424, which is commonly assigned to the assignee of the present application; and wherein the suture package is referred to as an RSO package (Reduced Size Organizer).

In the specific design of the flat tray-shaped plastic container having a peripheral channel as disclosed in the above-mentioned patent, the suture package is basically constituted of a rectangular round-cornered and flat-bottomed injection-molded plastic tray having a flat central surface area including a raised needle clamping structure formed thereon for engaging and "parking" a plurality of needles in a predetermined spaced array. Sutures each have one end thereof attached to each of the respective needles so as to form so-called "armed sutures". The sutures extend from each of the needles into a channel extending about the perimeter or periphery of the suture tray and are conducted into the channel so as to be essentially wound within the circumferential confines of the suture tray. The plurality of sutures which are positioned within the suture tray channel are protected against inadvertent outward displacement therefrom through the presence of a multiplicity of contiguously positioned resilient fingers which are integrally molded with the suture tray, and which project outwardly above the confines of the channel along a major portion of the length of the channel and, collectively, form a so-called "zipper structure" in which the inherently resilient nature of the fingers facilitates their temporary raising up to enable the introduction of the sutures into the suture tray channel by means of a suitable suture winding apparatus.

Although the rotary dial or turntable apparatus of the packaging machine pursuant to the foregoing U.S. patents provide for the packaging of armed sutures; in effect, needles with attached sutures, in a rapid and fully automated manner, such as by supplying the tray-shaped packages; thereafter parking the plurality of armed sutures in the packages, applying covers and removing the completed suture packages from the machine in a sequential station-to-station procedure, the machine was designed to primarily produce suture packages each containing a plurality of armed sutures.

SUMMARY OF THE INVENTION

Pursuant to the present inventive concept, the above-mentioned automated packaging machine is further improved upon in a novel and unique manner in that the machine is adapted to produce suture packages each containing a single armed suture, such packages being frequently in demand rather than packages containing a plurality of needles and sutures. Thus, in order to provide for high production rates which are essentially compatible with those employed in the manufacture of suture packages each containing a plurality of armed sutures, the present invention contemplates the provision of a fully automated packaging machine with a considerably increased rate of operating speed and production capability so as to render the packaging machines economically viable in comparison with the previously described automated packaging machine, while maintaining structural and functional reliability and ease of construction and maintenance.

Specifically, the automated packaging machine is supplied with empty suture trays each adapted to receive a single surgical needle and attached suture from a carousel containing a plurality of stacks of empty trays. The trays are sequentially sliced off or withdrawn from the bottom of a stack of trays and deposited on a rotary plate from which the trays are successively picked up and transferred through the intermediary of pivotable robotic arm structure to the automated packaging machine.

In order to attain the essentially automated packaging of singly-packaged or individual surgical needles with attached sutures, the automated packaging machine pursuant to the invention sets forth the provision of a rotary turret or dial-like turntable having a plurality of tool nests each possessing a suture tray supporting surface, with each tool next being circumferentially spaced about the turntable so as to be uniformly distributed about the periphery thereof. The rotary turret is rotated to cause the tool nests supporting packaging trays to be indexed forwardly so as to advance through a plurality of successive workstations which are adapted to, respectively, effectuate the supplying of each of the trays located on the tool nests or support surfaces with a single or individual surgical needle and attached suture, winding the suture into the confines of each needle and suture-containing tray, forming a latching engagement between a tray cover and the tray; and thereafter conveying each completed suture package to a station for removal from the machine and transfer to stacking bins or the like.

Operatively communicating in synchronism with the indexing rotation of the rotary turret is the carousel device housing the stacks of trays, which is adapted to supply empty trays sliced or separated from the bottom of a respective stack of the trays to a rotatable platform, and includes the operative robotic pivot arm structure to successively remove the trays from the rotatable platform and mount the empty trays on successive tool nests so as to be oriented in a vertical plane facing radially outwardly of the rotary turret. Thereafter, each tray is indexed sequentially forwardly by the rotary turret to a workstation which will impart movement to a portion of the tool nest having the tray supported thereon, whereby the tray remains oriented essentially vertically it is rotated angularly relative to the horizontal plane of rotation of the rotary turret. This movement enables a transfer device with a needle and suture swaying mechanism processing needle grippers at a further workstation to insert and position a surgical needle with its attached suture into a therewith aligned tray for retentive engagement with needle-engaging structure formed in the tray so as to grip and park the needle therein, with the suture extending from the needle and depending downwardly therefrom outwardly of the tray. The needle and suture-containing tray is then advanced forwardly on its respective tool nest to successive workstations responsive to indexed advance of the rotary turret wherein, at a first suture winding station, structure operatively cooperating with the tray and the tool nest supporting the tray imparts an initial rotational movement to the tray about an axis perpendicular to the plane of the while maintaining tray the depending suture under tension, and at a second subsequent winding station imparts a rapid winding motion to the tray over multiple predetermined rotations so as to fully wind the downwardly depending suture into a peripheral tray channel extending within the perimeter of the tray.

Thereafter, the tool nest mounting the tray with the needle parked therein and the attached suture which has been wound into the peripheral channel of the tray is advanced to a further workstation responsive to indexed rotation of the rotary turret; at which workstation an operating mechanism causes a bottommost cover to be sliced or separated from a stack of covers and transferred to a rotatable platform. The cover is then engaged by a robotically-controlled pivot arm which, under the action of a vacuum, pivots the cover into a vertical orientation and applies the cover onto the tray while concurrently imparting pressure to the cover to cause cooperating latching structure to clampingly fasten the cover to the needle and suture-containing tray. Upon completion of the cover-attaching sequence, the resultingly completed suture package is indexed to a further workstation at which suitable vacuum grippers on a pivot arm mechanism engages the suture package, and the suture package is disengaged from the tool nest on which it is supported and transferred to and stacked in repository or receiving units to be readied for further processing, such as sterilizing, overwrapping or the like, as may be required.

The foregoing sequence of operative steps is continually repeated for each successive tool nest on the rotary turret or turntable sequentially receiving empty trays from the carousel, while preceding tool nests each mounting a tray are conveyed through the above-mentioned packaging cycle. Thus, a successive tray is always placed into a position of readiness at a following or subsequent workstation and processed in a similar manner as before described during the forward indexing motion of the rotary turret or turntable. This ensures a continuously repetitive packaging cycle for successive suture packages in a highly efficient and high-speed operation without the need for any manual intervention in the operation of the packaging machine.

Intermediate various of the workstations as set forth hereinbefore; there may be arranged other workstations incorporating sensors adapted to enable ascertaining the presence of empty trays at the initial workstation, for a verification of a needle having been inserted into the trays and for inspection of the trays subsequent to the winding of the sutures into the tray channels; checking for the application of the covers to the trays, and facilitating the possible ejection of incomplete trays or the removal from the machine of defective packages.

Accordingly, it is an object of the present invention to provide novel package feed arrangement in an automated packaging machine, with the arrangement sequentially feeding individual package trays to successive tool nest on a rotary dial having a plurality of circumferentially spaced tool nests mounted thereon, so as to facilitate the trays to be subsequently supplied with armed sutures and tray covers or labels and thereafter transported in a rapid sequence from the machine.

A more specific object of the invention resides in the provision of a package feed arrangement as described herein in which a carousel having stacks of package trays has the bottom-most tray of a respective stack of trays sliced or separated from the remaining stack of trays by a rotatably indexed plate member possessing tray-receiving recesses from which the trays are sequentially removed by a cam-controlled pivot arm and positioned on successive tool nests of a rotatable dial or turntable of the packaging machine.

A further object resides in the provision of operative structure which, upon a package tray having been positioned on a tool nest, will impart rotation to the tool nest and tray thereon so as to pivot the tray into an angular orientation within the plane of the tray to facilitate the subsequent positioning of a surgical needle with an attached suture into the tray.

Another object of the present invention resides in the provision of a method for successively supplying package trays to a rotary dial of an automated suture packaging machine which mounts a plurality of tool nests each supporting a package tray to facilitate the latter being supplied with surgical needles and attached sutures with the arrangement for feeding package trays as described herein.

BRIEF DESCRIPTION OF THE DRAWINGS

Reference may now be had to the following detailed description of a preferred embodiment of a package tray feed arrangement for the inventive automated packaging machine for the packaging of surgical needles and attached sutures, taken in conjunction with the accompanying drawings; in which:

FIG. 3 illustrates a top plan view of the machine frame of FIG. 2;

FIGS. 13 and 14 illustrate, respectively, plan and side views, shown partly in section, of the rotatable plate member for separating trays from the carousel of FIG. 12;

FIG. 18 illustrates sensor-mounting structure for detecting and verifying the presence of a tray on a tool nest.

DETAILED DESCRIPTION OF THE PREFERRED EMBODIMENT

Figure 1:
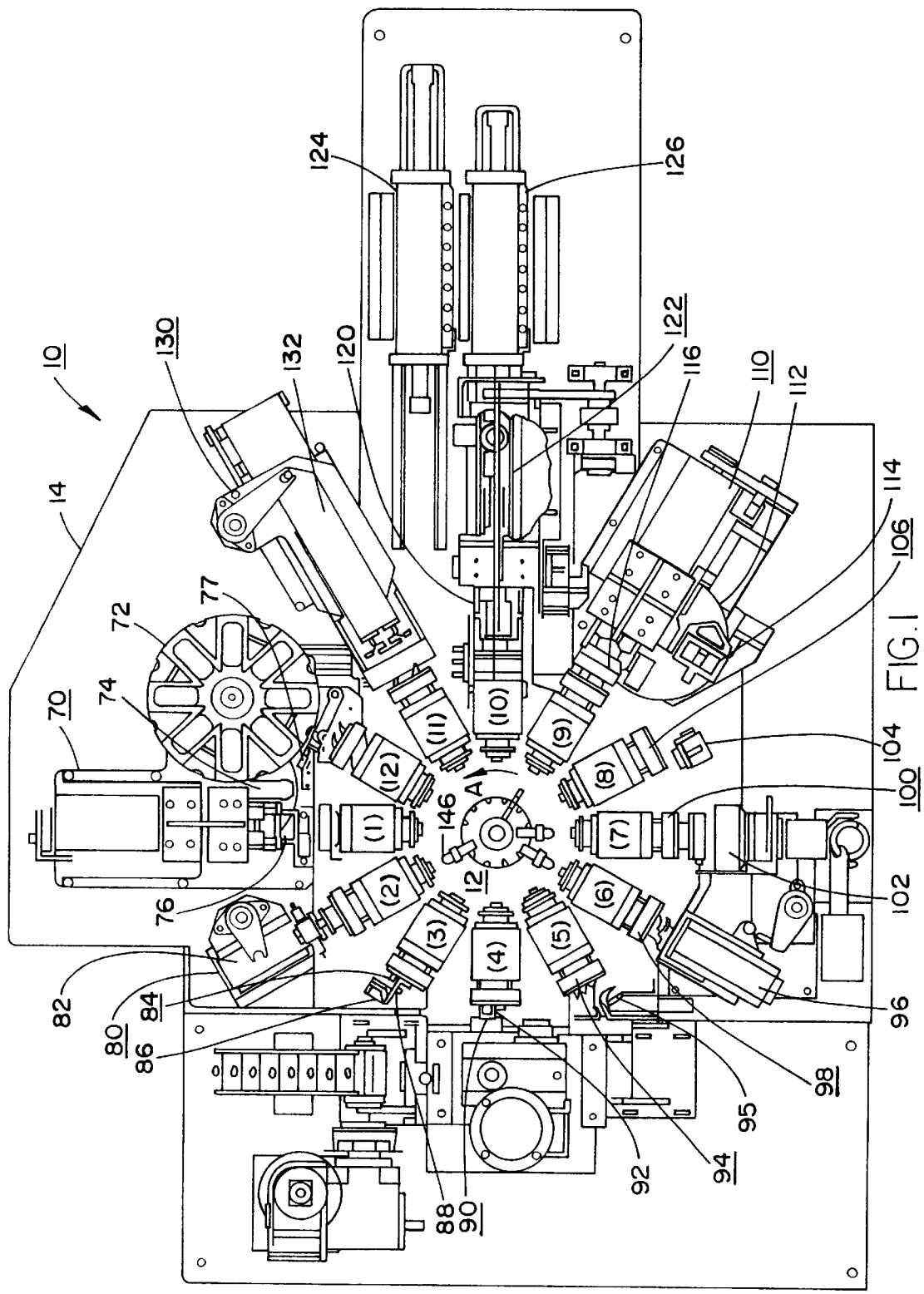
FIG. 1 illustrates generally diagrammatically, a plan view of the machine for the automated packaging of individual surgical needles and attached sutures, pursuant to the present invention.
Figure 2:
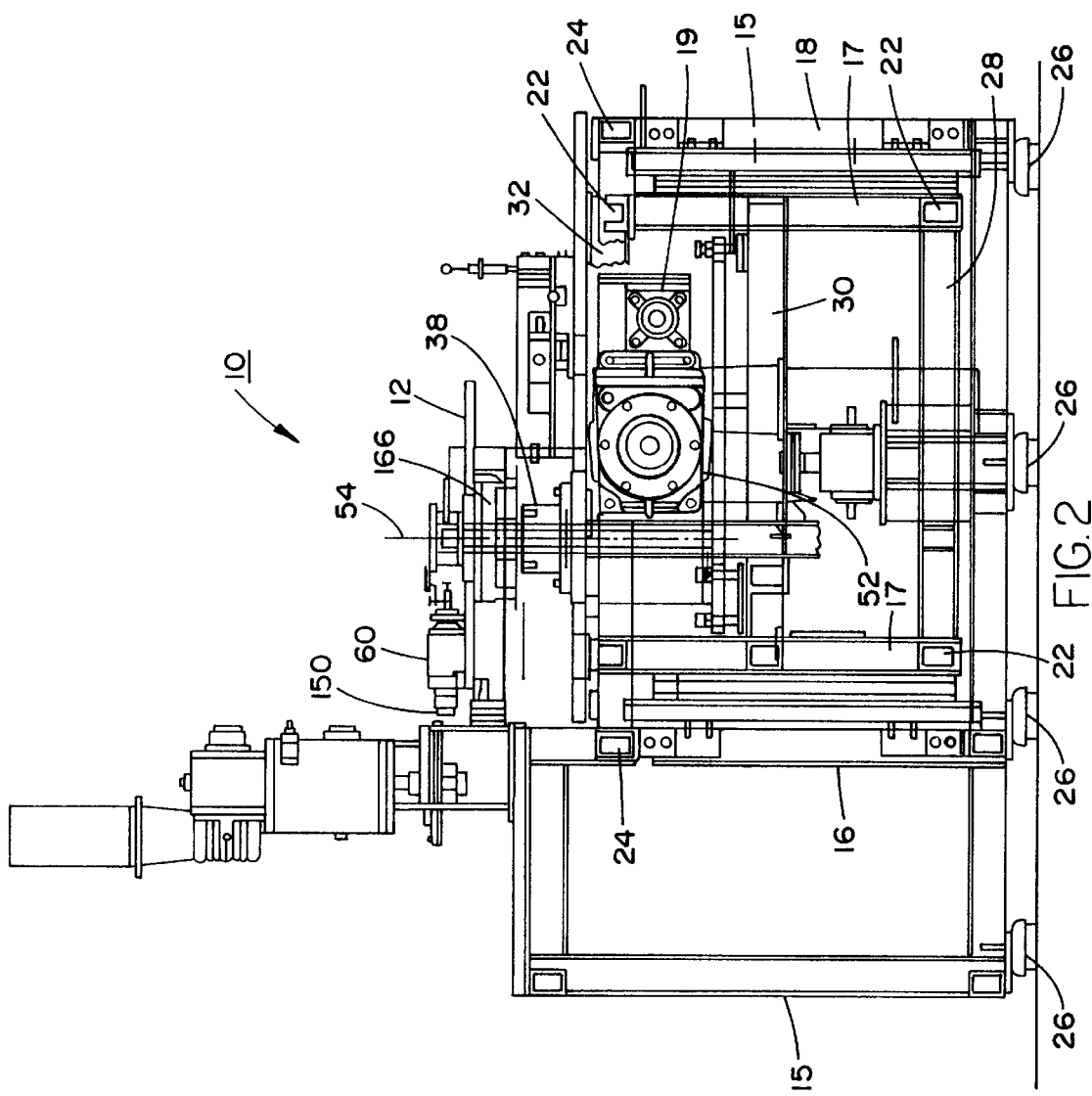
FIG. 2 illustrates a side elevational view of the machine frame of FIG. 1.

Referring now in more specific detail to the drawings, FIGS. 1 to 3 illustrate, in a generally diagrammatic plan view, the automated needle and suture packaging machine 10 pursuant to the invention. The machine 10 comprises a rotary turret or turntable 12 which is essentially a packaging dial supported on an essentially stationary machine frame structure 14.

The rigid frame structure 14, as illustrated in FIGS. 2 and 3, basically includes structural uprights 16 and 18, which are interconnected by horizontal beams 20, 22, 24, with the entire frame structure 14 adapted to be supported on a floor through the intermediary of adjustable leveling footings 26. The frame structure 14 comprises an outer stationary frame arrangement 15, and an inner vertically adjustable frame arrangement 17 comprising horizontal beams 28, 30 and 32, and vertical beams 34, 36 interconnected therewith supporting the turntable 12 for vertical adjustment relative to the stationary machine frame components. The vertical adjustment of the frame arrangement 17 is provided for by a central servo motor actuated jack screw 38, which also concurrently effectuates the vertical adjustment of all of the operative packaging devices at the various workstations of the machine so as to accommodate the packaging of a wide range of differently sized surgical needles without the necessity for modifying any machine components. Arranged within the frame structure are the various belt drives 40, 42, 44, 46 and 48 and operating drive components 50 for the machine, and the vacuum-generating systems 52 employed in the packaging cycles for the suture packages, as described hereinbelow. The turntable 12 is oriented in a horizontal plane, and through the intermediary of a program-controlled drive installation, is rotatable in an indexing or incrementally angular advance about a central vertical axis 54. In this instance, during operation of the machine, the turntable 12 is rotated in a counter-clockwise direction when viewed from above, as represented by arrow A, so as to be advanced in 30° increments.

The rotary turret or turntable 12 is essentially constituted of a circular disk-shaped member or packaging dial which has a plurality of tool nests 60 mounted thereon. The tool nests 60 are mounted in a circumferentially uniformly spaced array on the upper surface of the package dial or rotary turret 12, and with each tool nest 60 having an outer end projecting radially outwardly of the peripheral edge of the turret or dial 12, as described hereinbelow.

In this particular construction of the packaging machine 10, by way of example, twelve (12) tool nests 60 are arranged at uniformly distributed annular spacings of 30° from each other about the circumference of the dial or rotary turret 12.

In essence, as mentioned hereinbelow, the rotary turret or turntable 12 of the packaging machine 10 is adapted to be indexed forwardly in an angularly incremental or indexed rotational advance, each such incremental advance comprising one-twelfth of the 360° circumferential rotation of the turntable, or basically 30°, along the direction of rotation identified by arrow A in FIG. 1, such that the tool nests 60 which are each adapted to mount a suture tray or package are designed to be advanced in sequence to a number of successive workstations; designated herein as workstations (1) through (12), which are stationarily evenly spaced about the periphery of the rotary turret 12, as illustrated in FIG. 1 of the drawings.

The successive workstations which collectively constitute the automated machine 10 for the packaging of surgical needles and attached sutures are essentially briefly described as follows; viewed in the direction of rotation of arrow A:

(1) A first workstation 70 relates to the operative aspect of empty suture package trays being successively separated from the bottom of stacks of trays contained in a rotary carousel 72 to be transferred onto a rotationally indexed plate 74 under the action of a vacuum, and thereafter picked up and transferred by a cam-controlled robotic pivot arm structure 76 to successive tool nests 60 so as to be retained thereon while being conveyed by the rotary turret or dial 12 to subsequent workstations, as set forth hereinbelow.

(2) At this workstation 80, to which the respective tool nest 60 supporting the empty tray thereon has been advanced by the rotational advance of the turntable 12 mounting the tool nest; in effect, indexed 30° forwardly; operative slide-controlled pivot structure 82 engages a plate element on the outer end of the tool nest 60 which supports the empty tray under a vacuum, and rotates the plate element and tray counterclockwise within the vertical plane thereof about a horizontal radial axis of the tool nest 60 through an angle of approximately sixteen and one-half (16.5°) degrees so as to be in appropriate angular orientation relative to a horizontal axis for facilitating the subsequent insertion and retention of a surgical needle and attached suture into the tray.

(3) This workstation 84 provides for a sensor 86 which is mounted stationarily on a bracket arrangement 88 and faces the tool nest 60 so as to be able to check for the presence of an empty tray on the tool nest. The sensor 86 is suitably aimed at a black spot present on the packaging tooling nest, and in the absence of a tray being positioned thereon, enables deactivating the forward advance of the turntable 12 and concurrently may emit a signal to alert personnel regarding the missing tray.

(4) The next workstation 90 along the rotational path of motion of the turntable in the direction of arrow A, provides gripper mechanism 92 for inserting a single surgical needle and a therewith attached suture into the suture tray which has been indexed forwardly by the rotary turret 12 so as to be located in operative alignment with the needle-feed mechanism. The needles are conveyed by a mechanism so as to be mounted on suitable clamping or needle "park" structure constituting an integral portion of the tray. Vacuum-controlled suture capture and tensioning devices which are located below each tool nest 60, become operative at this workstation to capture and tension the suture portions depending outwardly and downwardly of the tray mounting the surgical needle.

(5) At this workstation 94, a stationary sensor 95 located radially outwardly of the turntable 12 may be utilized to ascertain the presence of a surgical needle and attached suture having been properly introduced into the tray at the previous workstation 90.

(6) A first tray winding mechanism 96 at this workstation 98 engages the plate element on the tool nest supporting the tray, while the suture capture and tensioning device ensures that the suture portion depending outwardly and downwardly from the tray is maintained under tension by a vacuum-operated tensioning device associated therewith, with the tray being rotated counterclockwise within its vertical plane through approximately 163.5°, to assume a horizontal orientation which is 180° inverse to its original orientation on the tool nest 60 at workstation (1), and with the remaining length of the suture being tensioned by the vacuum device externally of the tray.

(7) At a subsequent workstation 100, a further winding mechanism 102 engages the tool nest 60 and the tray mounted thereon, and imparts rapid rotation to the tray so as to enable tray structure engaging portions of the mechanism to introduce and completely wind the entire remaining length of the suture into a peripheral groove extending about the confines of the tray.

(8) A stationary sensor 104 at this workstation 106 is located radially outwardly of the turntable 12, and is adapted to ascertain the positioning of the surgical needle in th tray and that the entire length of the suture has been fully and appropriately wound into the peripheral groove of the tray.

(9) This workstation 110 provides apparatus for the application and attachment of a cover or label to the tray containing the surgical needle and attached suture to produce or complete suture to produce a complete suture package. A rotatably indexed disc-like plate 112 includes a plurality of equidistantly circumferentially spaced cover-receiving areas, these being rotated below a vertical stack 114 of covers or labels such that, under the action of a vacuum, the bottommost covers of the stack are sequentially sliced off or separated and deposited into a respective area of the plate under the influence of the vacuum present therebeneath, and thereafter rotated into radial alignment with a tool nest 60 mounting the tray containing the surgical needle and attached wound suture. A cam-controlled robotic pivot arm structure 116 lifts the cover from the plate, while a subsequent area receives a further cover from the stack for transfer onto a following tray, and pivots upwardly and extends horizontally forwardly so as to position the cover into latching engagement with the tray, thereby forming the completed suture package.

(10) A robotic pivotable gripper arm 120 removes the completed package from the tool nest 60 at this subsequent workstation 122, and swings downwardly so as to deposit the completed suture package into receiving bins or compartments within elongated tray members 124 whereby upon a certain amount of trays being deposited to fill the tray member the latter is indexed to align a further empty compartment of a tray member with the tool nests. The tray member having the various filled compartments is then conveyed to a storage unit 126 and replaced automatically by another empty tray member.

(11) In the event of a suture package being defective, such as having a cover lacking or misplaced, and the resultant package has accordingly not been removed at the preceding package unloading workstation 122; at this workstation 130 a reciprocating arm structure 132 has a gripper head which engages and removes the rejected packages from the tool nests, and deposits them onto a conveyor belt 134 for conveyance to a suitable waste disposal site.

(12) This final workstation on the packaging machine 10 is essentially an "empty" or operatively unutilized location along the path of travel of turntable or dial 12, with the carousel of the workstation (1) being located in proximity therewith primarily for purposes of convenience and accessibility.

Figure 6:
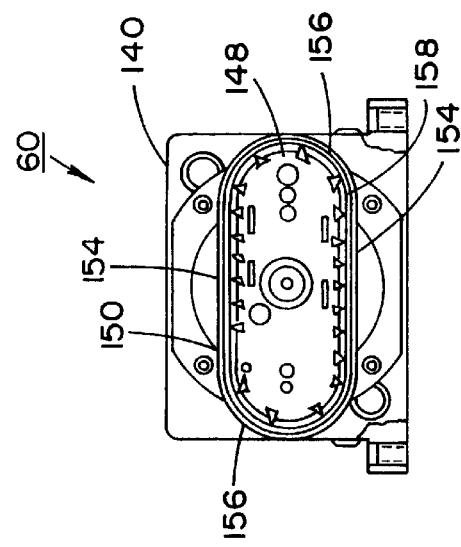
FIGS. 4, 5 and 6 illustrate, respectively, partially-sectional side and top plan views and a front end view of a tool nest utilized in the machine of FIG. 1.
Figure 4:
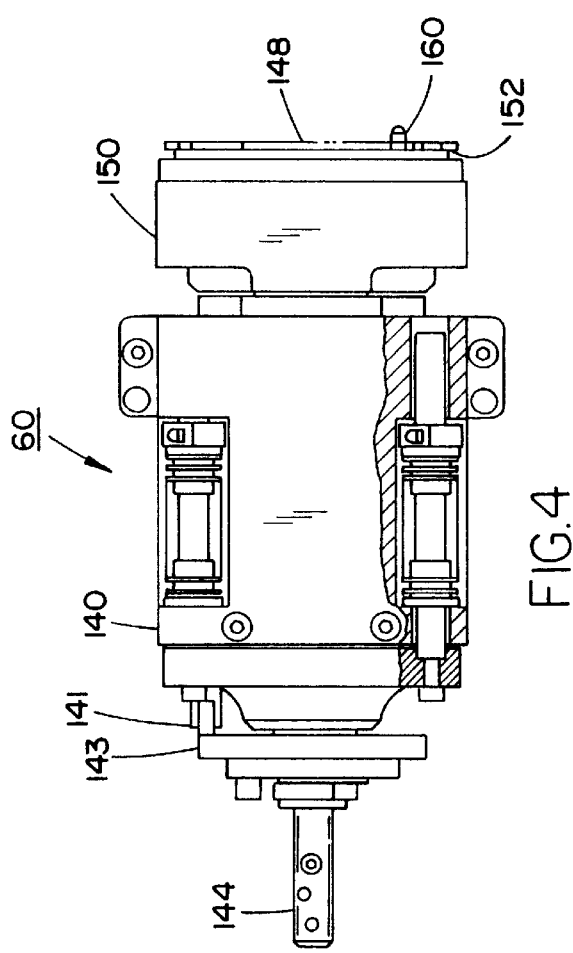
Figure 5:
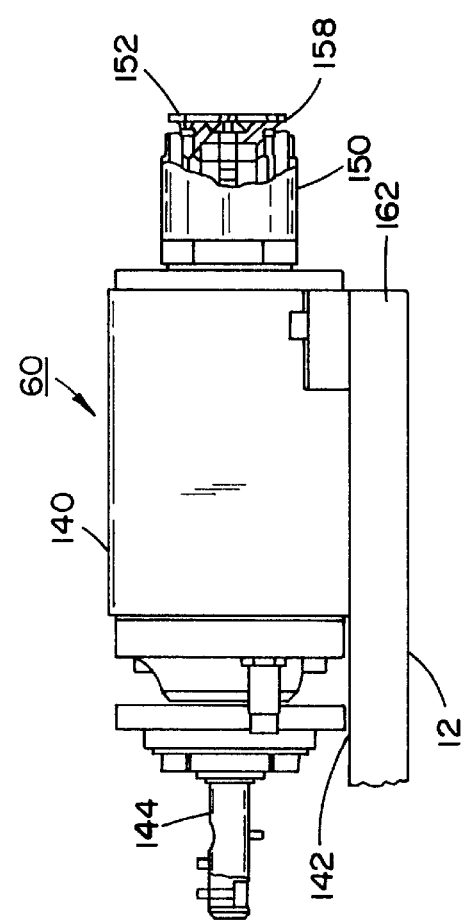

As shown in FIGS. 4 through 6, each tool nest 60 includes a housing 140 which is fixedly mounted on the upper surface 142 of the rotary turret 12. Each housing 142 includes a horizontal radially extending central through bore having a shaft 144 rotatably journaled therein. The shaft 144 is normally secured against rotation within housing 140; however, at predetermined workstations of the machine, the shaft 144 may be released by means of an air-operated motor (not shown) so as to be rotatable and axially radially inwardly movable within housing 140 against stationary cam structure 146 mounted centrally on the rotary turret or dial 12 for regulating the rotational displacement which may be imparted to the shaft 144, as discussed hereinbelow in more specific detail.

The radially outwardly facing structure 148 of a plate element 150, which is fixedly secured to the radially outer end of shaft 144, is adapted for supporting suture package components, and particularly the package trays which are utilized in the production of surgical needle and attached suture-containing packages.

In essence, the radially outer structure of the tool nest housing 140 for mounting suture trays includes the plate element 150 which comprises an elongate vertically oriented plate member 152 having generally parallel opposite sides 154 and convexly rounded opposite ends 156 so as to be generally in conformance with the peripheral shape of a package tray. An external planar surface on the plate member 152 includes protruding perimeter or rim structure 158 for seating engagement therein of a suture tray, with the plate member 152 being fixedly secured to the radially outer end of the shaft 144 so as to be adapted for rotation therewith. Extending forwardly from the external planar surface of the rotatable plate member 152 of the tool nest 60 are protuberances or guide pins 160 which are intended to align the package tray thereon for appropriate positioning on the plate member 152, with the tray adapted to be retained thereon through the application of a vacuum to the exterior plate member surface through passageways communicating with a vacuum source connected thereto through the tool nest housing 140.

Figure 7:
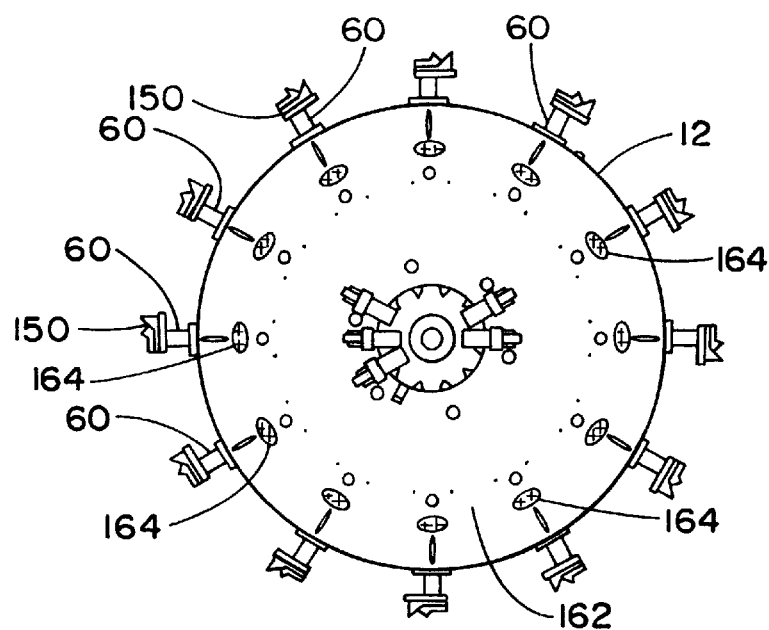
FIG. 7 illustrates a bottom view of the dial or turntable mounting the tool nests, showing vacuum ports for communicating the tool nests with vacuum-generating source means.
Figure 8:
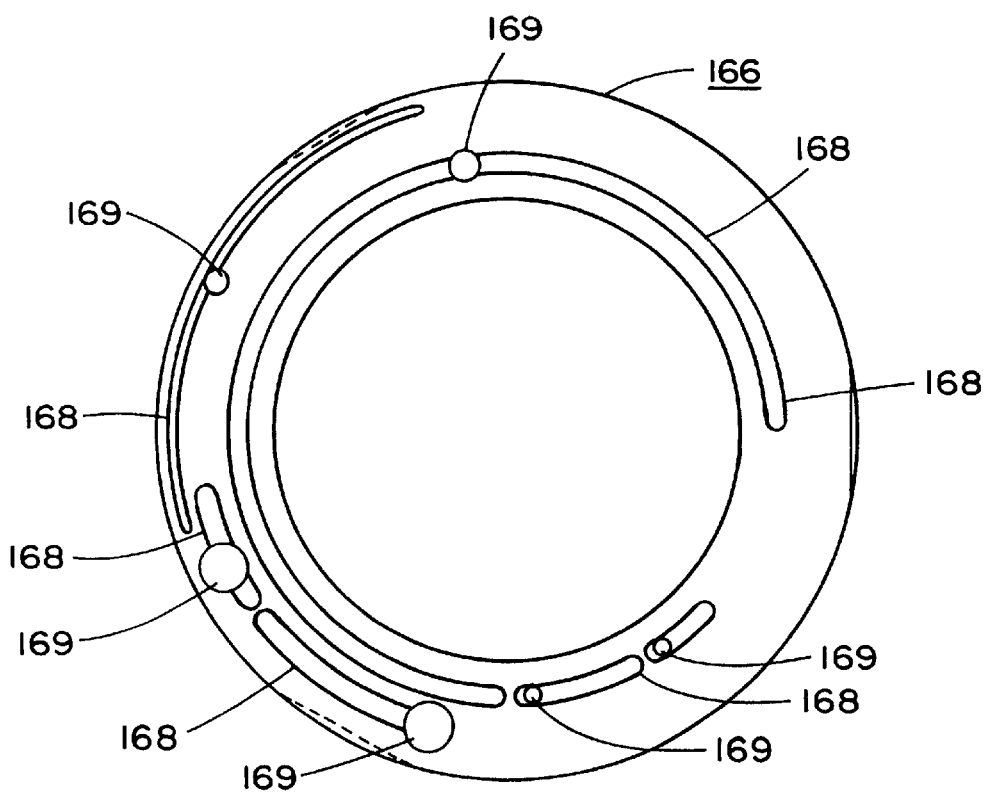
FIG. 8 illustrates a vacuum plenum for supplying the tool nests with controlled vacuum conditions.

The vacuum passageways extend through the lower surface 162 of the dial or turntable 12, as shown in FIG. 7, which includes a plurality of apertures 164 each communicating with, respectively, passageways leading to an associated tool nest 60. The vacuum is supplied to the apertures 164 in a selective controlled mode through the intermediary of a stationary vacuum plenum 166 arranged below the dial 12, as shown in FIG. 2 of the drawings. The plenum 166, as shown in FIG. 8, includes outlet slots 168 and ports 169 for applying or closing a vacuum to respective tool nests 60 in accordance with the rotational positions of the dial 12 with the aperture or ports 164 in the lower surface 162 being in communication with the vacuum plenum outlet slots or ports.

Reverting now to the aspect of the invention which is particularly concerned with the package tray feeding installation, in essence, at workstation 70 (1), wherein empty suture package trays or bases are applied onto the tool nests 60 of the automated packaging machine 10, reference may be specifically had to FIGS. 10 through 14 of the drawings.

Figure 9:
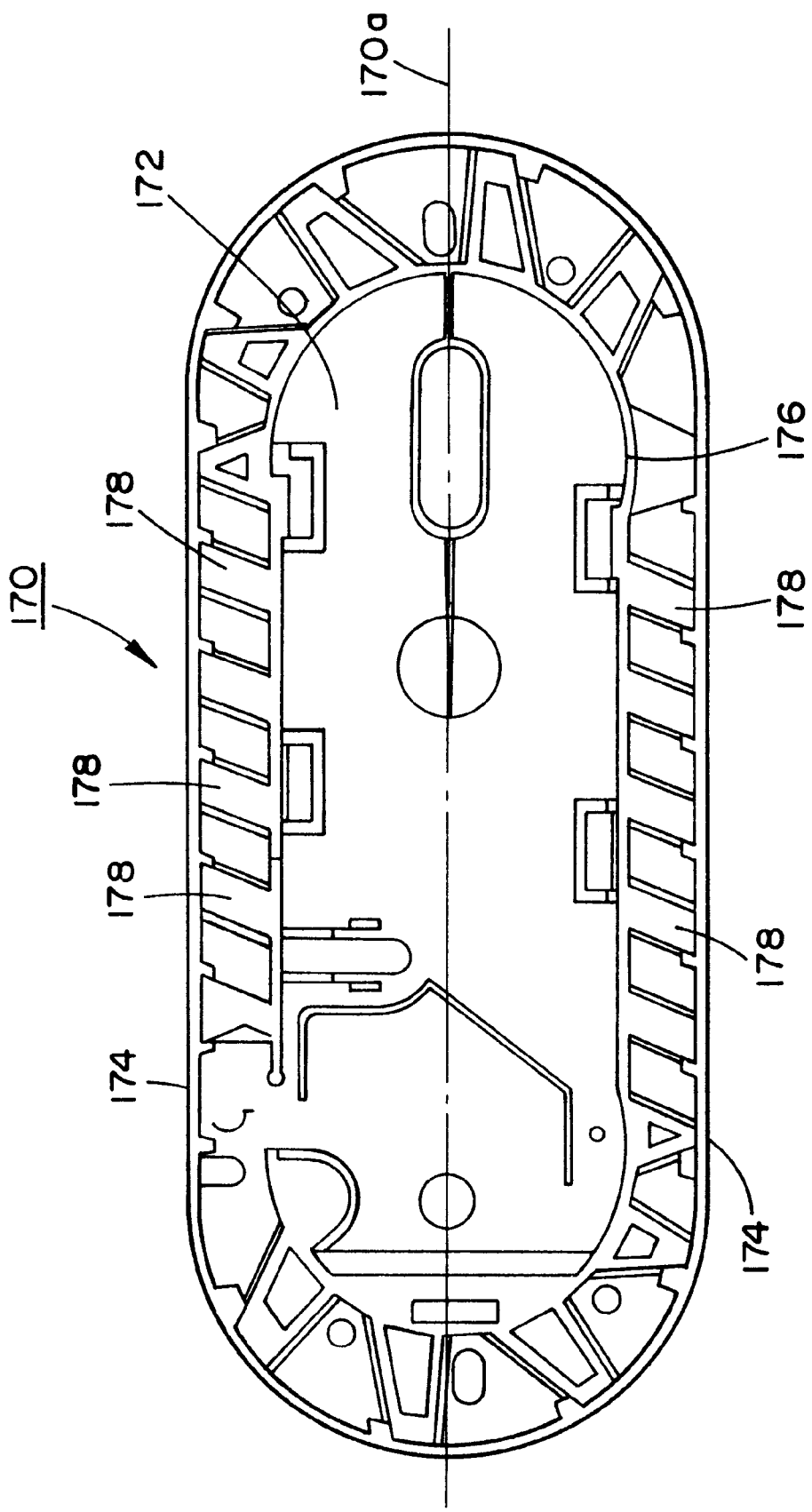
FIG. 9 illustrates a packaging tray for the packaging of an individual surgical needle and attached suture.

The suture package tray 170, as shown in FIG. 9 of the drawings, is essentially constituted of molded plastic material, and includes a planar base 172 with parallel sides and semi-circular rounded ends. A vertical wall 174 extends about the perimeter of the tray, while inwardly spaced thereof is a second vertical wall 176 having radially outwardly extending fingers 178 which are flexible at the upper edge reaching close to the outer wall 174 so as to define a hollow channel structure. Apertures and surgical needle engaging structure is molded into the tray, as more specifically disclosed in copending U.S. patent appln. Ser. No. 08/521,978; filed Aug. 31, 1995 (Attorney Docket ETH-1088; D-9570), the disclosure of which is incorporated herein by reference, and which is commonly assigned to the assignee of this application.

In essence, arranged adjacent the rotary dial or turntable 12, the latter of which is supported on the vertically adjustable frame arrangement 17, as shown in FIGS. 2 and 3, and which dial 12 mounts twelve tool nests 60 in uniform circumferentially spaced relationship, so as to enable the rapid provision of successive tool nests 60 with trays 170 having a shape as shown in FIG. 9; is the tray-loading installation 180. The installation, which is also supported on the adjustable frame structure 17, includes the rotatable carousel 72 which has eight (8) vertical chutes 182 arranged in an adjoining spoke-like annular array about a vertical control shaft 184. Each chute 182 is adapted to hold a vertical stack of superimposed empty package trays 170, as shown in the drawings. The carousel 72 is adapted to be rotatably indexed about shaft 184 through the intermediary of a suitable drive mechanism 186 whereby one of the chutes at any one time, which is filled with a stack of the trays 170, is adapted to have the open bottom end thereof located in close proximity above-the upper surface 188 of a circular or disc-like plate 190. The plate 190 is arranged beneath the lower end of the carousel 72 with a surface portion thereof extending below the bottom end of the chute 182 of the carousel which is most closely adjacent thereto. The circular rotary plate 190, as shown in FIGS. 13 and 14 has four radially extending depressions or recesses 192, each being of a depth essentially corresponding to the height of the vertical wall 174 and peripheral shape of the package tray 170, and with each recess 192 being at a 90° angular spacing relative to an adjacent recess. Each recess 192 has an aperture 194 in its bottom surface 196 communicating with a passageway 198 leading to a controllable vacuum generating arrangement within the packaging machine 10.

Between the chute 182 and the disc-like plate 190 is a single multi-tray buffer area 193 which contains a buffer stack of trays 170. After a chute 182 is empty, the buffer area 193 allows time for the next chute 182 of the rotatable carousel 72 to be indexed into position without stopping the machine. Therefore, trays 170 can be continuously fed into the disc-like plate 190 from the buffer stack of trays 170 without interrupting the packaging process.

When one of the recesses 192 of the rotary plate 190 is in alignment with the buffer stack of trays 170 in the buffer area 193, a bottommost tray 170 in the buffer stack is sliced off or separated from the remaining buffer stack of trays and deposited in the recess 192 located therebeneath under the effect of a vacuum which is applied to the bottom surface 196 of the recess 194.

Figure 10:
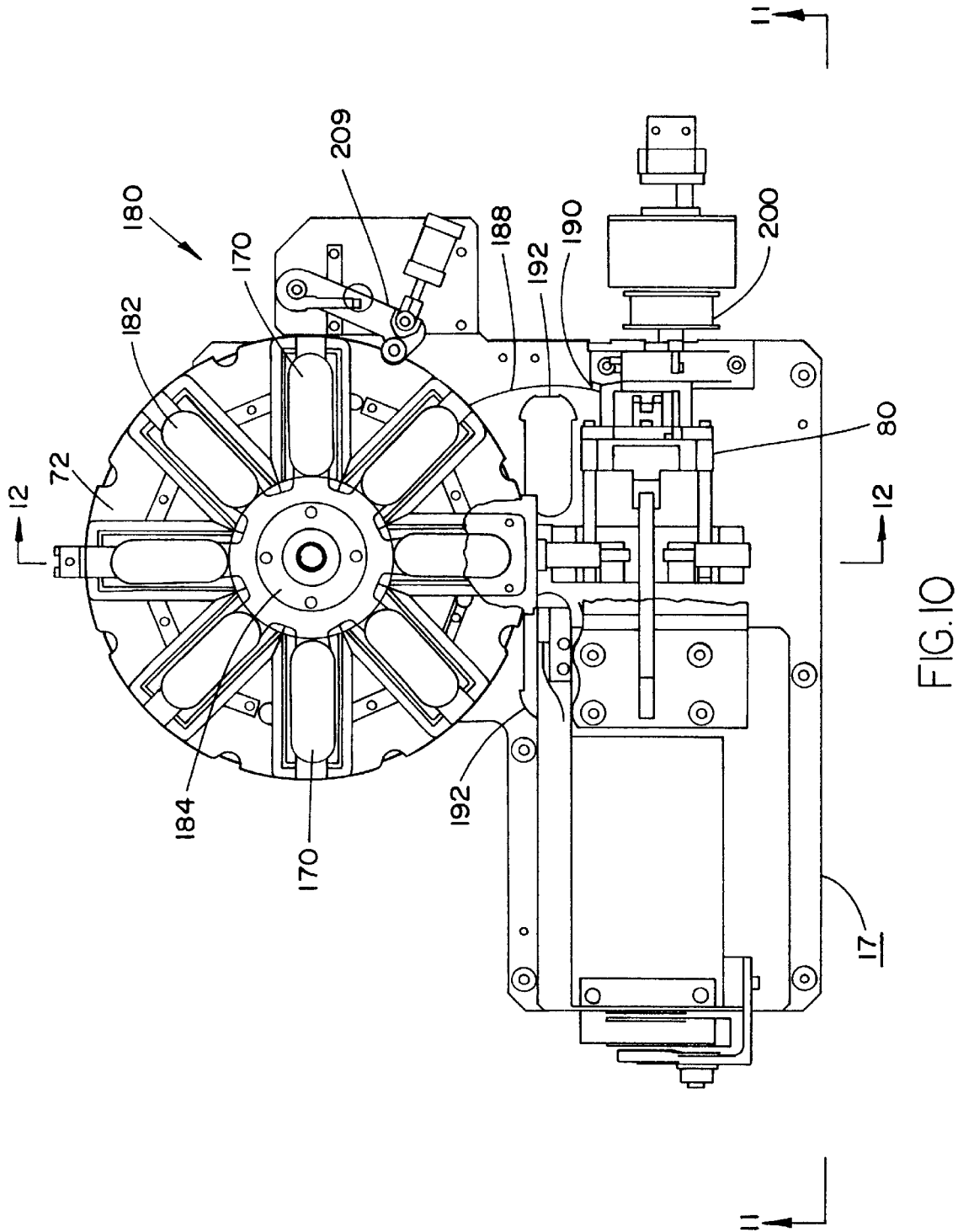
FIG. 10 illustrates a top plan view of the carousel and robotic pivot-arm arrangement of the tray loading and feeding workstation of the packaging machine.
Figure 11:
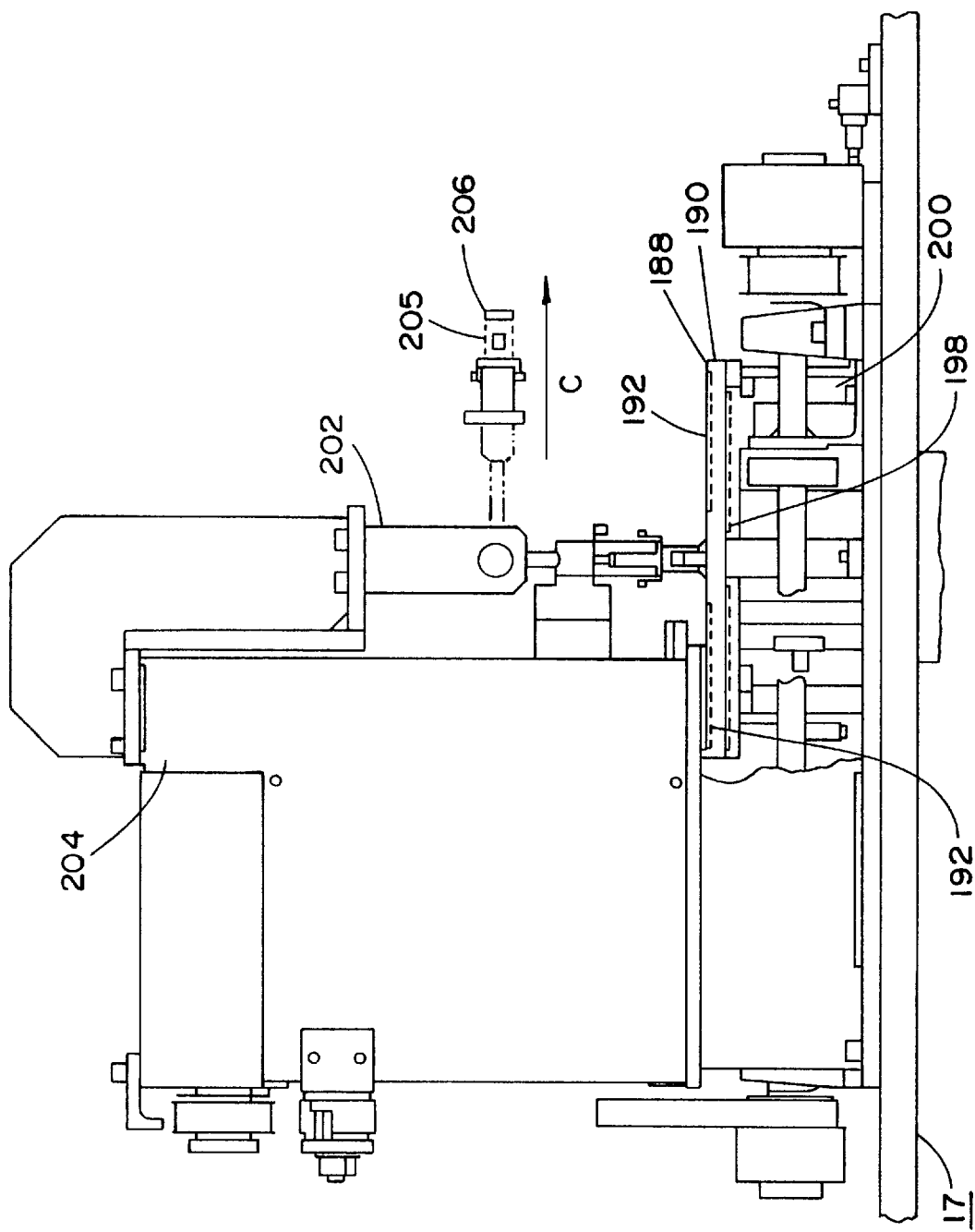
FIG. 11 illustrates an elevational side view taken along line 11—11 in FIG. 10.
Figure 12:
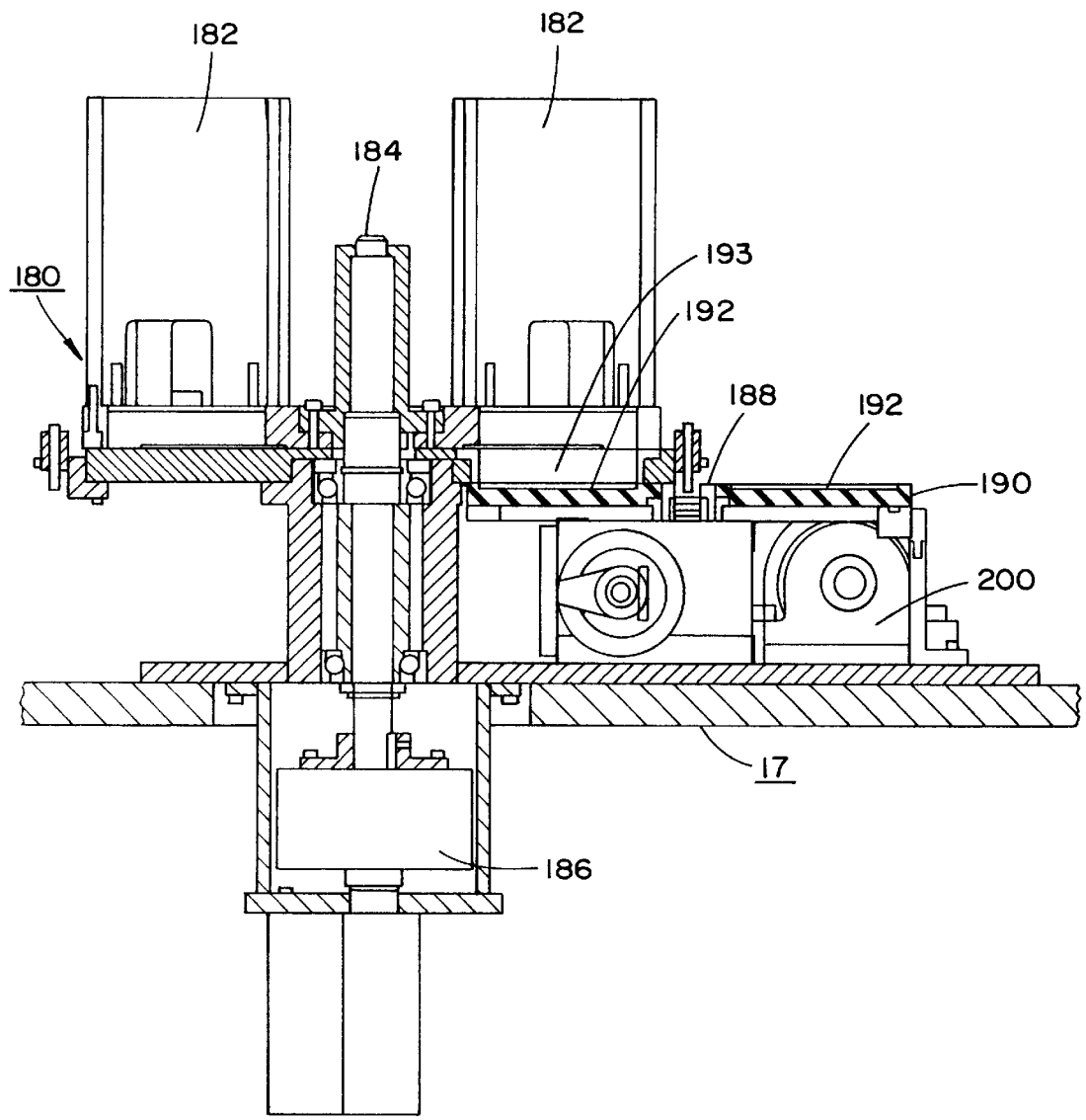
FIG. 12 illustrates, on an enlarged scale, a sectional view taken along line 12—12 in FIG. 10.

As the plate 190 is rotatably indexed forwardly by means of a drive unit 200, each successive recess 192 has a successive bottommost tray 170 deposited therein from the buffer area 193 which is in superimposed alignment therewith. As the plate 190 continues its indexed rotation, a robotic or camcontrolled pivot arm 202 mounted in housing structure 204, as shown in FIGS. 10 and 11, has vacuum or suction elements 205 located at a forward end 206 depending downwardly so as to contact the tray 170 located in recess 192 on plate 190. The vacuum is released in the recess 192, and a vacuum applied to elements 205 to cause the tray 170 to adhere thereto. The pivot arm 202 is then pivoted upwardly into a horizontal orientation, as shown in FIG. 11, and then extended forwardly along arrow C to cause the bottom surface of the tray 170 carried thereon to come into contact with the tray-receiving surface on the vertical plate element 150 of a therewith aligned tool nest 60 on the rotary turntable 12.

Thereupon, the pivot arm 202 has the vacuum released from elements 205, while a vacuum is applied to plate element 150 to resultingly cause the tray 170 to be assumed and retained thereon. The pivot arm 202 is then retracted and pivoted downwardly, as shown in FIG. 11, so as to engage a successive tray 170 positioned in the next recess 192 in the plate 190, and thereafter, in synchronism with the forwardly indexed rotation of the turntable 12 in a direction of arrow A, repeat the foregoing cycle of positioning trays 170 on the plate elements 150 of successive tool nests 60 coming into operative alignment with the robotic pivot arm structure 202.

As the chute 182 of the carousel 72 which is located above plate 190 empties of trays 170, upon the last remaining tray 170 of the stack of trays in that chute 182 being transferred to the rotary plate 190, the carousel 72 is rotatably indexed forwardly by an indexing mechanism 209 to the next or adjacent tray-filled chute 182, so as to now have that tray-filled chute 182 arranged in superposed alignment with the rotary plate 190 and to enable the uninterrupted continuing supplying of empty trays 170 to the recesses 192 in rotary plate 190, and thereafter through the intermediary of the repetitive cycles of operation of robotic pivot arm member 202 to the tool nests 60 on the turntable 12 of the automated packaging machine 10. The empty chutes 182 on the carousel 72 may be manually refilled with new stacks of package trays 170, as required.

Thereafter, the tool nest 60 with the tray 170 retained under a vacuum on the radially outwardly facing surface the plate element 150, which is at a generally horizontal orientation of the longitudinal axis 170a of the tray 170 defined by the walls 174, with the vacuum being generated in the installation through vacuum plenum 166 communicating with plate element 150 through the dial 12 and housing 140, is then advanced to workstation 80 at (2) through the indexed advance of the turntable 12 (a rotation of 300 in the direction of arrow A).

Figure 15:
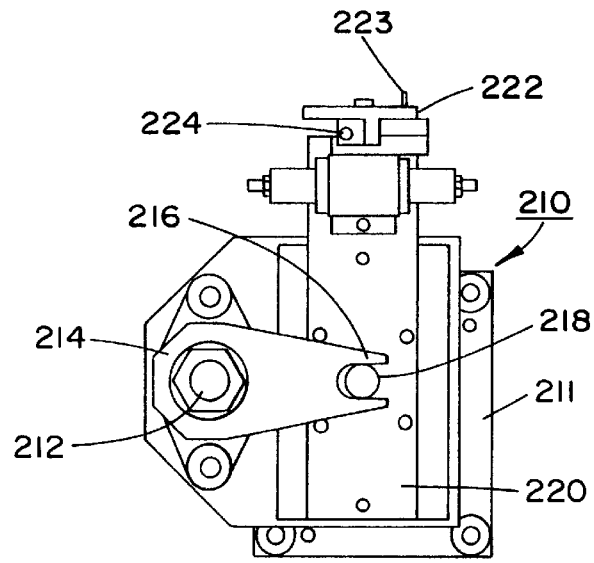
FIGS. 15, 16 and 17 illustrate, respectively, plan, end and side views of an apparatus for imparting an angular displacement or tilted orientation to trays supported on the tool nests.
Figure 17:
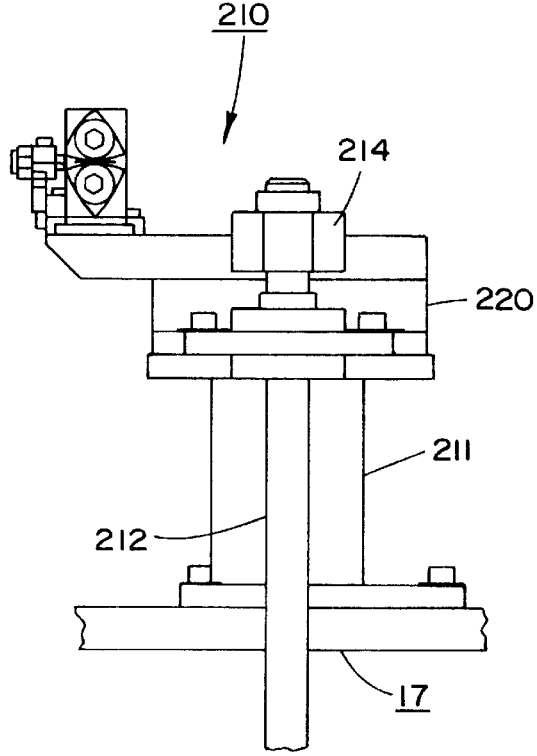
Figure 16:
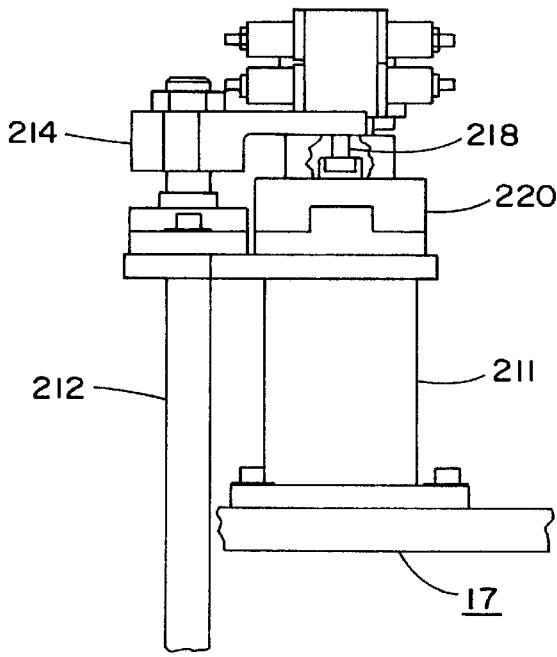

An apparatus 210 at this workstation (2), as shown in FIGS. 15 through 17, which is intended to impart a tilt to the tray 170 about its axis 170a, includes bracket structure 211 mounted on the frame 17 of machine 10. A vertical pivot shaft 212 has the lower end thereof connected to a device for oscillating the shaft about its vertical axis. The upper end of shaft 212 connects to a lever arm 214 having a bifurcated distal end 216 which engages a trunnion or pin 218 fixed mounted on a reciprocably slidable element 220 supported on the bracket 211. The forward end 222 of element 220 which is located proximate to a therewith aligned tool nest 60 which has a tray 170 positioned on plate element 150, includes protruding structure 223 for engagingly contacting the tray 170 and plate element 150 when the element 220 is advanced towards the tool nest 60.

A cooperating arm element 224 is adapted to be activated so as to impart a counterclockwise rotation to the tray 170 and plate element 150 within the vertical plane thereof about the axis of the shaft 144 in the tool nest mounting the plate element 150. The tray 170 is angled or tilted counterclockwise (facing the front thereof) relative to the initially horizontally oriented longitudinal axis 170a through an angle of about 16.5°, so as to be in a ready position for the insertion therein of an armed suture; i.e. a surgical needle and attached suture at a subsequent workstation.

In order to be able to effectuate the rotational movement or tilted displacement of the tray 170, an air-operated motor in housing 140 is activated so as to cause shaft 144 to retract radially into contact with a cam 230 of a stationary cam structure 146 on dial or turntable 12. This releases shaft 144 for rotation by disengaging locking pins 141 at the radially inward end of housing 140 until the plate element 150 and tray 170 are tilted by shaft 144 as required, i.e. 16.5° relative to the horizontal. The air motor 116 then deactivates and causes the shaft 144 to slide axially forwardly, allowing the pins 141 to engage corresponding bore in locking plate 143, and locking the plate element 150 and tray 170 into the tilted position.

Thereafter, upon the tool nest 60 having the element 150 with the tilted tray 170 therein being advanced forwardly through the indexed rotation of the turntable 12, to workstation 84 at (3), an upright support stationary structure 230 includes at its upper end a bracket 230 supporting a sensor 232 for detecting and verifying the presence of a tray 170 on the plate element 150 of the tool nest 60; for instance, by scanning a spot which may be formed at a specific location on the surface of tray 170. The tray 170 is now in readiness to have a needle and attached suture inserted therein at subsequent workstation 90 (4); as described in detail in copending application Ser. No. 09/020,091.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A package feed arrangement in a machine for the automated packaging of a single needle having an attached suture to produce a suture package, wherein said machine includes automatically winding said suture within the confines of a tray and attaching a cover to said tray so as to constitute said suture package, said machine having at least one tool nest for supporting said tray, and means for imparting a forwarding motion to said tool nest and said tray supported thereon for indexed advance to a plurality of workstations stationarily arranged proximate the path of advancing movement of said at least one tool nest; said package feed arrangement comprising:

(a) a first workstation including means for mounting an empty said tray on a support surface located on said at least one tool nest, said means comprising means for stacking a supply of said empty trays; a rotary plate arranged beneath said tray stacking means, said tray stacking means comprising a carousel having at least two open-bottomed chutes in a circular rotatable arrangement, each chute having a vertical stack of said trays arranged therein, said rotary plate extending closely below the bottom of said chutes so as to receive the bottommost tray therefrom on an upper surface of said rotary plate; means for indexing said rotary plate forwardly at predetermined angular increments; motion means for engaging said tray on said rotary plate and transferring said tray to the support surface on said one tool nest; and a buffer area disposed adjacent to said upper surface of said rotary plate and containing at least said bottommost tray such that upon a chute being emptied of said trays, an adjacent tray-filled chute is rotated into position above said rotary plate to facilitate the supplying of said bottommost tray to said rotary plate without interrupting the indexing of the rotary plate.

2. An arrangement as claimed in claim 1, wherein said rotary plate is in communication with a vacuum-generating source for imparting a vacuum to the upper surface of said rotary plate to retain said tray thereon during at least the indexing advance of said rotary plate.

3. An arrangement as claimed in claim 1, wherein said motion means comprises pivotable arm structure having tray-engaging means for lifting said tray from said rotary plate and transferring said tray to the support surface on said at least one tool nest.

4. An arrangement as claimed in claim 3, wherein said rotary plate communicates with a vacuum-generating source for imparting a vacuum thereto for retaining said tray on said plate, said vacuum being released upon said tray-engaging means contacting said tray, and a vacuum in said tray-engaging means retaining said tray thereon to facilitate transporting said tray to the support surface on said at least one tool nest.

5. An arrangement as claimed in claim 4, wherein upon said tray-engaging means mounting said tray on the support surface of said at least one tool nest, said vacuum in said tray-engaging means is released and a vacuum concurrently applied to the support surface of said at least one tool nest so as to retain said tray thereon.

6. An arrangement as claimed in claim 1, wherein said motion means comprises a cam-controlled robotic pivot arm adapted to swing between a vertical orientation to a horizontal and forward motion for transferring said tray from said rotary plate to said support surface on said at least one tool nest.

7. An arrangement as claimed in claim 1, wherein a second workstation includes means for imparting a predetermined angular displacement to said tray and support surface on said at least one tool nest mounting said tray to facilitate subsequent insertion of a surgical needle into said tray.

8. An arrangement as claimed in claim 7, wherein said means for imparting said angular displacement comprises structure for engageable contact with said support surface.

9. An arrangement as claimed in claim 8, wherein said structure comprises a slidable element having contact means for engaging said support surface, and pivot arm means for imparting movement to said contact means towards said support surface to impart said angular displacement thereto.

10. An arrangement as claimed in claim 7, wherein said support surface on said at least one tool nest is fastened to a rotatable shaft extending through said at least one tool nest; means normally securing said shaft from relative rotation, said means releasing said shaft for axial movement and rotation in said at least one tool nest to facilitate said angular displacement means to impart said angular displacement to said tray and support surface.

11. An arrangement as claimed in claim 10, wherein cam structure is contacted by an opposite end of said shaft to limit the axial movement of said shaft.

12. An arrangement as claimed in claim 1, wherein said at least one tool nest includes locking pin means for locking said tray and support surface in said angularly displaced position.

13. An arrangement as claimed in claim 7, wherein said angular displacement of said tray and support surface on said at least one tool nest subtends an angle of about 16.5° with a horizontal axis of said tray.

14. An arrangement as claimed in claim 1, wherein a plurality of said tool nests are mounted on a turntable, said workstations being spaced about said turntable.

15. A method for feeding a package in a machine for the automated packaging of a single needle having an attached suture to produce a suture package, wherein said machine includes automatically winding said suture within the confines of a tray and attaching a cover to said tray so as to constitute said suture package, said machine having at least one tool nest for supporting said tray, and imparting a forwarding motion to said tool nest and said tray supported thereon for indexed advance to a plurality of workstations stationarily arranged proximate the path of advancing movement of said at least one tool nest; said package feeding method comprising:

(a) at a first workstation mounting an empty said tray on a support surface located on said at least one tool nest; stacking a supply of said empty trays; arranging a rotary plate arranged beneath said stacked trays, said stacked trays being arranged on a carousel having at least two open-bottomed chutes in a circular rotatable arrangement, each chute having a vertical stack of said trays arranged therein, said rotary plate extending closely below the bottom of said chutes so as to receive the bottommost tray therefrom on an upper surface of said rotary plate, indexing said rotary plate forwardly at predetermined angular increments; effectuating engaging said tray on said rotary plate, transferring said tray to the support surface on said one tool nest, and arranging a buffer area adjacent to said upper surface of said rotary plate and containing at least said bottommost tray such that upon a chute being emptied of said trays, an adjacent tray-filled chute is rotated into position above said rotary plate to facilitate the supplying of said bottommost tray to said rotary plate without interrupting the indexing of the rotary plate.

16. A method as claimed in claim 15, wherein said rotary plate is in communication with a vacuum-generating source for imparting a vacuum to the upper surface of said rotary plate to retain said tray thereon during at least the indexing advance of said rotary plate.

17. A method as claimed in claim 15, wherein said tray engaging is carried out by pivotable arm structure having tray-engaging structure for lifting said tray from said rotary plate and transferring said tray to the support surface on said at least one tool nest.

18. A method as claimed in claim 17, wherein said rotary plate communicates with a vacuum-generating source for imparting a vacuum thereto for retaining said tray on said plate, said vacuum being released upon said tray-engaging means contacting said tray, and a vacuum in said tray-engaging means retaining said tray thereon to facilitate transporting said tray to the support surface on said at least one tool nest.

19. A method as claimed in claim 18, wherein upon said tray being mounted on the support surface of said at least one tool nest, said vacuum in said tray-engaging structure is released and a vacuum concurrently applied to the support surface of said at least one tool nest so as to retain said tray thereon.

20. A method as claimed in claim 15, wherein a cam-controlled robotic pivot arm adapted to swing between a vertical orientation to a horizontal and forward motion for transferring said tray from said rotary plate to said support surface on said at least one tool nest.

21. A method as claimed in claim 15, wherein at a second workstation there is imparted a predetermined angular displacement to said tray and support surface on said at least one tool nest mounting said tray to facilitate subsequent insertion of a surgical needle into said tray.

22. A method as claimed in claim 21, wherein imparting said angular displacement is effected by a structure in engageable contact with said support surface.

23. A method as claimed in claim 22, wherein said structure comprises a slidable element having a contact for engaging said support surface, and a pivot arm for imparting movement to said contact towards said support surface to impart said angular displacement thereto.

24. A method as claimed in claim 21, wherein said support surface on said at least one tool nest is fastened to a rotatable shaft extending through said at least one tool nest; said shaft being normally secured against relative rotation, said shaft being released for axial movement and rotation in said at least one tool nest to facilitate said angular displacement being imparted to said tray and support surface.

25. A method as claimed in claim 24, wherein cam structure is contacted by an opposite end of said shaft to limit the axial movement of said shaft.

26. A method as claimed in claim 15, wherein said at least one tool nest includes at least one locking pin for locking said tray and support surface in said angularly displaced position.

27. A method as claimed in claim 21, wherein said angular displacement of said tray and support surface on said at least one tool nest subtends an angle of about 16.5° with a horizontal axis of said tray.

28. A method as claimed in claim 15, wherein a plurality of said tool nests are mounted on a turntable, said workstations being spaced about said turntable.

* * * * *